(12) United States Patent
Yamamoto et al.

(10) Patent No.: US 7,470,549 B2
(45) Date of Patent: Dec. 30, 2008

(54) MEASUREMENT METHOD USING BIOSENSOR

(75) Inventors: Masayoshi Yamamoto, Kanagawa (JP); Toshihide Ezoe, Kanagawa (JP); Nobuhiko Ogura, Kanagawa (JP); Katsumi Hayashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 394 days.

(21) Appl. No.: 11/137,390

(22) Filed: May 26, 2005

(65) Prior Publication Data
US 2006/0003395 A1 Jan. 5, 2006

(30) Foreign Application Priority Data
May 26, 2004 (JP) .............................. 2004-155605
Sep. 27, 2004 (JP) .............................. 2004-279358

(51) Int. Cl.
*G01N 33/543* (2006.01)
(52) U.S. Cl. .................. 436/518; 385/12; 385/129; 385/130; 422/55; 422/57; 422/82.01; 422/82.05; 422/82.11; 435/287.2; 435/287.9; 435/288.7; 435/808; 436/164; 436/165; 436/524; 436/525; 436/527; 436/805; 436/806
(58) Field of Classification Search .................. 385/12, 385/129, 130; 422/55, 57, 82.01, 82.05, 422/52.11; 435/287.2, 287.9, 288.7, 808; 436/164, 165, 518, 524, 525, 527, 805, 806
See application file for complete search history.

(56) References Cited

U.S. PATENT DOCUMENTS

| 4,240,889 A | * | 12/1980 | Yoda et al. ............. 204/403.09 |
| 4,844,613 A | * | 7/1989 | Batchelder et al. .......... 356/318 |
| 5,242,828 A | | 9/1993 | Bergström et al. |
| 5,492,840 A | * | 2/1996 | Malmqvist et al. .......... 436/518 |
| 5,641,640 A | | 6/1997 | Hanning |
| 5,965,456 A | * | 10/1999 | Malmqvist et al. .......... 436/514 |
| 6,589,798 B1 | | 7/2003 | Löfås |
| 6,808,938 B2 | | 10/2004 | Hämäläinen et al. |

FOREIGN PATENT DOCUMENTS

JP            200262297 A    *    2/2002

* cited by examiner

*Primary Examiner*—Christopher L Chin
(74) *Attorney, Agent, or Firm*—Sughrue Mion, PLLC (57) ABSTRACT

It is an object of the present invention to provide a method for simultaneously carrying out the detection or measurement of a substance interacting with a physiologically active substance immobilized on a biosensor and the analysis of the effects of the above substance on the biological activity of the physiologically active substance. The present invention provides a method using a biosensor formed by immobilizing a physiologically active substance on a substrate, wherein the detection and measurement of a substance interacting with said physiologically active substance and the measurement of the biological activity of said physiologically active substance are carried out on said single biosensor.

14 Claims, 2 Drawing Sheets

MEASUREMENT METHOD USING BIOSENSOR

TECHNICAL FIELD

The present invention relates to a measurement method using a biosensor. More specifically, the present invention relates to a method for carrying out on a single biosensor the detection or measurement of a substance interacting with a physiologically active substance immobilized on such a biosensor and the measurement of the biological activity of the above physiologically active substance. Further, the present invention relates to a screening method using a biosensor. More specifically, the present invention relates to a method for screening a test substance, which is characterized in that it conducts both the detection or measurement of a substance interacting with a physiologically active substance immobilized on a biosensor and the measurement of the biological activity of the above physiologically active substance.

BACKGROUND ART

Recently, a large number of measurements using intermolecular interactions such as immune responses are being carried out in clinical tests, etc. However, since conventional methods require complicated operations or labeling substances, several techniques are used that are capable of detecting the change in the binding amount of a test substance with high sensitivity without using such labeling substances. Examples of such a technique may include a surface plasmon resonance (SPR) measurement technique, a quartz crystal microbalance (QCM) measurement technique, and a measurement technique of using functional surfaces ranging from gold colloid particles to ultra-fine particles. The SPR measurement technique is a method of measuring changes in the refractive index near an organic functional film attached to the metal film of a chip by measuring a peak shift in the wavelength of reflected light, or changes in amounts of reflected light in a certain wavelength, so as to detect adsorption and desorption occurring near the surface. The OCM measurement technique is a technique of detecting adsorbed or desorbed mass at the ng level, using a change in frequency of a crystal due to adsorption or desorption of a substance on gold electrodes of a quartz crystal (device). In addition, the ultra-fine particle surface (nm level) of gold is functionalized, and physiologically active substances are immobilized thereon. Thus, a reaction to recognize specificity among physiologically active substances is carried out, thereby detecting a substance associated with a living organism from sedimentation of gold fine particles or sequences.

A measurement chip commonly used in the surface plasmon resonance (SPR) measurement comprises a transparent substrate (e.g., glass), an evaporated metal film, and a thin film having thereon a functional group capable of immobilizing a physiologically active substance. The measurement chip immobilizes the physiologically active substance on the metal surface via the functional group. A specific binding reaction between the physiological active substance and a test substance is measured, so as to analyze an interaction between biomolecules. As a thin film having a functional group capable of immobilizing a physiologically active substance, there has been reported a measurement chip where a physiologically active substance is immobilized by using a functional group binding to metal, a linker with a chain length of 10 or more atoms, and a compound having a functional group capable of binding to the physiologically active substance (Japanese Patent No. 2815120). Moreover, a measurement chip comprising a metal film and a plasma-polymerized film formed on the metal film has been reported (Japanese Patent Laid-Open No. 9-264843).

As stated above, the detection or measurement of a substance interacting with a physiologically active substance immobilized on a measurement chip has been carried out in the conventional surface plasmon resonance (SPR) measurement. However, since the measurement of the biological activity of the above physiologically active substance has not been carried out, it has been impossible to analyze whether or not such a substance interacting with the physiologically active substance affects the biological activity of the above physiologically active substance.

DISCLOSURE OF THE INVENTION

It is an object of the present invention to solve the above-mentioned problems of the prior art techniques. In other words, it is an object of the present invention to provide a method for simultaneously carrying out the detection or measurement of a substance interacting with a physiologically active substance immobilized on a biosensor and the analysis of the effects of the above substance on the biological activity of the physiologically active substance. It is another object of the present invention to provide a method for screening a test substance by detecting or measuring a substance interacting with a physiologically active substance immobilized on a biosensor, and also by analyzing the effects of the above substance on the biological activity of the physiologically active substance.

As a result of intensive studies directed towards achieving the aforementioned objects, the present inventors have found that the aforementioned object can be achieved by using a single biosensor formed by immobilizing a physiologically active substance on a substrate to carry out both the detection or measurement of a substance interacting with the above physiologically active substance and the measurement of the biological activity of the above physiologically active substance. Further, the present inventors have found that that the aforementioned object can be achieved by the screening of a test substance by carrying out the detection or measurement of a substance interacting with a physiologically active substance using a biosensor formed by immobilizing the above physiologically active substance on a substrate, and further carrying out the measurement of the biological activity of the above physiologically active substance. The present invention has been completed based on these findings.

Thus, the present invention provides a measurement method using a biosensor formed by immobilizing a physiologically active substance on a substrate, wherein the detection and measurement of a substance interacting with said physiologically active substance and the measurement of the biological activity of said physiologically active substance are carried out on said single biosensor.

Preferably, the physiologically active substance is a protein. More preferably, the physiologically active substance is an enzyme.

Preferably, the detection or measurement of a substance interacting with the physiologically active substance is carried out by surface plasmon resonance analysis.

Preferably, the surface plasmon resonance analysis is carried out by using a biosensor used for a surface plasmon resonance measurement device comprising: a dielectric block; a metal film formed on a face of the dielectric block; a light source for generating a light beam; an optical system for allowing said light beam to enter said dielectric block such that total reflection conditions can be obtained at the interface between said dielectric block and said metal film and that components at various incident angles can be contained; and a light-detecting means for detecting the state of surface plasmon resonance by measuring the intensity of the light beam totally reflected at said interface, said biosensor being comprised of said dielectric block and said metal film, wherein said dielectric block is formed as one block comprising the entirety of the entrance face and exit face of said light beam and a face on which said metal film is formed, said metal film is integrated with the dielectric block.

Preferably, the measurement of the biological activity of the physiologically active substance is carried out by spectroscopic measurement.

Preferably, the measurement method according to the present invention comprises:
(1) a step of allowing a test substance to come into contact with a biosensor formed by immobilizing a physiologically active substance on a substrate;
(2) a step of detecting or measuring the interaction between the physiologically active substance and the test substance; and
(3) a step of measuring the biological activity of the physiologically active substance in the presence of the test substance.

Further, the present invention provides a method for screening a test substance, which comprises:
(1) a step of allowing a test substance to come into contact with a biosensor formed by immobilizing a physiologically active substance on a substrate, so as to detect the test substance interacting with said physiologically active substance by surface plasmon resonance analysis or local plasmon resonance analysis; and
(2) a step of measuring the biological activity of said physiologically active substance in the presence of said test substance.

Preferably, 1 to 10 molecules of the test substances bind to a single molecule of the physiologically active substance.

Preferably, the detection of a plurality of test substances by surface plasmon resonance analysis or local plasmon resonance analysis is carried out in a parallel detection approach.

Preferably, the immobilization of a physiologically active substance on a biosensor and the detection of a test substance interacting with said physiologically active substance is carried out at different positions.

Preferably, a test substance interacting with the physiologically active substance is detected by surface plasmon resonance analysis or local plasmon resonance analysis based on any of a binding amount, a binding constant, a binding rate constant, or a dissociation rate constant.

Preferably, the biological activity of the physiologically active substance is indicated as any of a receptor activity level, an enzyme activity level, an antibody activity level, a metabolism activity level, a membrane potential, an ion emission level, or a gene expression level.

Preferably, virtual screening is carried out on test substances before step (1), so as to reduce the number of test substances to be subjected to screening.

Preferably, screening is automatically carried out using a screening device to which a standard value has previously been inputted.

In figures, 10 indicates measurement unit; 11 indicates dielectric block; 12 indicates metal film; 13 indicates sample-retaining frame; 14 indicates sensing substance; 31 indicates laser light source; 32 indicates condenser; 40 indicates photodetector; S40 indicates output signal; 400 indicates guide rod; 401 indicates slide block; 402 indicates precision screw; 403 indicates pulse motor; 404 indicates motor controller; 410 indicates unit connected body; and 411 indicates connecting member.

BEST MODE FOR CARRYING OUT THE INVENTION

The embodiments of the present invention will be described below.

The present invention relates to a measurement method using a biosensor formed by immobilizing a physiologically active substance on a substrate, wherein the detection and measurement of a substance interacting with said physiologically active substance and the measurement of the biological activity of said physiologically active substance are carried out on said single biosensor. By carrying out both the detection or measurement of a substance interacting with the physiologically active substance immobilized on the biosensor and the measurement of the biological activity of the above physiologically active substance on a single biosensor, it becomes possible to determine whether or not a test substance binding to the physiologically active substance has bound to the active site thereof, for example. Thus, the effects of the test substance on the biological activity of the physiologically active substance can simultaneously be analyzed.

The method for screening a test substance according to the present invention is characterized in that it comprises: (1) a step of allowing a test substance to come into contact with a biosensor formed by immobilizing a physiologically active substance on a substrate, so as to detect the test substance interacting with the physiologically active substance by surface plasmon resonance analysis or local plasmon resonance analysis; and (2) a step of measuring the biological activity of the above physiologically active substance in the presence of the test substance. In the present invention, by carrying out both the detection or measurement of a substance interacting with a physiologically active substance and the measurement of the biological activity of the above physiologically active substance, it becomes possible to determine whether or not a test substance binding to a physiologically active substance has bound to the active site of the physiologically active substance, for example, thereby analyzing the effects of the test substance on the biological activity of the physiologically active substance. It is to be noted that local plasmon (localized surface plasmon) is plasmon existing in a fine metal particle or at the tip of a metal needle. The size of a region in which the local plasmon is localized is almost the same as the size of a fine particle or a needle tip. Thus, the size can be determined to be significantly smaller than the wavelength of light. Since the frequency of local plasmon strongly depends on the form of a fine particle or the type of a metal atom, the scattering spectrum varies among fine particles. A physiologically active substance (a protein or the like) is immobilized on the surface of a fine particle, and a test substance binding to the physiologically active substance can be analyzed through changes in the scattering spectrum.

Figure 3:
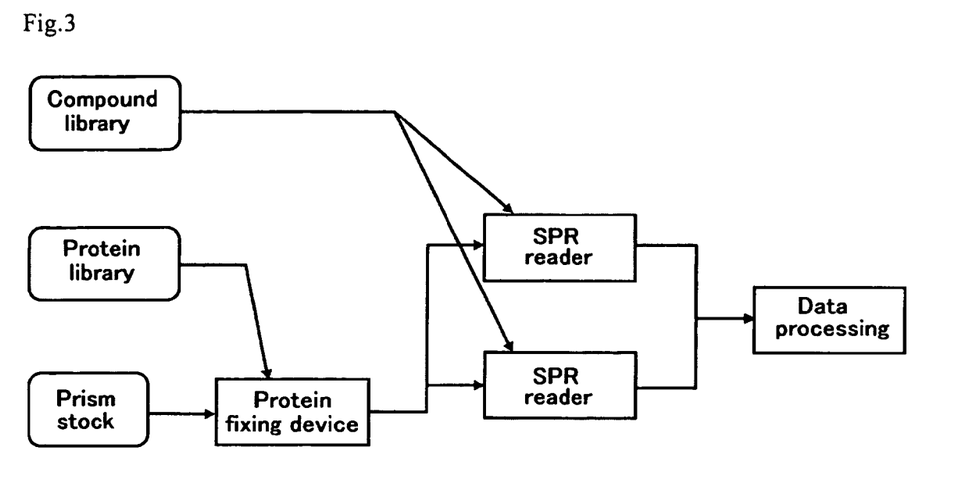
FIG. 3 shows an example of SPR system for carrying out the screening method of the present invention.

In the present invention, a physiologically active substance is converted into a solid phase. In order to solidify a physiologically active substance, known methods are applied. In addition, a unit for solidifying a physiologically active substance such as a protein is preferably separated from a unit for measuring the interaction between the solidified physiologically active substance and a test substance. An example of the structure of a device used for carrying out the screening of the present invention is shown in FIG. 3. By separating a unit for solidifying a protein from a unit for measuring interaction, the ability to measure such interaction is significantly improved. Moreover, as shown in FIG. 3, in the present invention, the detection of a plurality of test substances by surface plasmon resonance analysis or local plasmon resonance analysis can preferably be carried out in a parallel detection approach.

The number of test substances to be screened in the present invention is preferably 1,000 or more, more preferably 10,000 or more, and further preferably 100,000 or more.

The type of a test substance used in the present invention is not particularly limited, as long as it interacts with a physiologically active substance (ligand), which will be described later in the present specification. Examples of a test substance may include a low molecular weight organic compound, a high molecular weight compound, nucleic acid such as DNA, a protein (including an antibody or the like), a peptide or a fragment thereof, sugar, and amino acid.

In a preferred embodiment of the present invention, screening can automatically be carried out using a screening device to which a standard value has previously been inputted. That is to say, preferably, a standard value within a range capable of being selected (for example, a binding amount, a binding constant, a binding rate constant, a dissociation rate constant, or the like in the screening of a test substance interacting with a physiologically active substance; or a receptor activity level, an enzyme activity level, a metabolism activity level, a membrane potential, an ion emission level, a gene expression level, or the like in the case of the biological activity of a physiologically active substance) has been inputted in advance, and a test substance included within such a range is automatically selected. The selected test substance is preferably displayed such that it is visually differentiated in a display device. The method of visual differentiation is not particularly limited. Examples of such a method may include the size of letters, color, flashing letters, the color of letters, the use of underlines, and the use of frames.

The screening method of the present invention comprises: a first step of selecting a test substance interacting with a physiologically active substance; and a second step of measuring the biological activity of the physiologically active substance in the presence of the test substance selected in the first step. In the first step, it is preferable that test substances included in the selective range of a standard value that has previously been inputted in a device be automatically selected, and that the selected test substances be automatically measured in the second step. Thereafter, in the second step, it is preferable that test substances included in the selective range of a standard value (e.g. a receptor activity level, an enzyme activity level, a metabolism activity level, a membrane potential, an ion emission level, a gene expression level, etc.), which reflects the biological activity that has previously been inputted in the device, be automatically selected.

Moreover, in the present invention, virtual screening can be carried out on test substances before the aforementioned first step, so as to reduce the number of test substances to be subjected to screening.

The biosensor of the present invention has as broad a meaning as possible, and the term biosensor is used herein to mean a sensor, which converts an interaction between biomolecules into a signal such as an electric signal, so as to measure or detect a target substance. The conventional biosensor is comprised of a receptor site for recognizing a chemical substance as a detection target and a transducer site for converting a physical change or chemical change generated at the site into an electric signal. In a living body, there exist substances having an affinity with each other, such as enzyme/substrate, enzyme/coenzyme, antigen/antibody, or hormone/receptor. The biosensor operates on the principle that a substance having an affinity with another substance, as described above, is immobilized on a substrate to be used as a molecule-recognizing substance, so that the corresponding substance can be selectively measured.

In the biosensor used in the present invention, a metal surface or a metal film can be used as a substrate. A metal constituting the metal surface or metal film is not particularly limited, as long as surface plasmon resonance is generated when the metal is used for a surface plasmon resonance biosensor. Examples of a preferred metal may include free-electron metals such as gold, silver, copper, aluminum or platinum. Of these, gold is particularly preferable. These metals can be used singly or in combination. Moreover, considering adherability to the above substrate, an interstitial layer consisting of chrome or the like may be provided between the substrate and a metal layer.

The film thickness of a metal film is not limited. When the metal film is used for a surface plasmon resonance biosensor, the thickness is preferably between 0.1 nm and 500 nm, and particularly preferably between 1 nm and 200 nm. If the thickness exceeds 500 nm, the surface plasmon phenomenon of a medium cannot be sufficiently detected. Moreover, when an interstitial layer consisting of chrome or the like is provided, the thickness of the interstitial layer is preferably between 0.1 nm and 10 nm.

Formation of a metal film may be carried out by common methods, and examples of such a method may include sputtering method, evaporation method, ion plating method, electroplating method, and nonelectrolytic plating method.

A metal film is preferably placed on a substrate. The description "placed on a substrate" is used herein to mean a case where a metal film is placed on a substrate such that it directly comes into contact with the substrate, as well as a case where a metal film is placed via another layer without directly coming into contact with the substrate. When a substrate used in the present invention is used for a surface plasmon resonance biosensor, examples of such a substrate may include, generally, optical glasses such as BK7, and synthetic resins. More specifically, materials transparent to laser beams, such as polymethyl methacrylate, polyethylene terephthalate, polycarbonate or a cycloolefin polymer, can be used. For such a substrate, materials that are not anisotropic with regard to polarized light and having excellent workability are preferably used.

Preferably in the present invention, the substrate is a metal surface or metal film coated with a hydrophobic polymer or polyhydroxy polymer, or a metal surface or metal film having a self assembled membrane. The hydrophobic polymer, polyhydroxy polymer, and self assembled membrane are mentioned below.

The hydrophobic polymer used in the present invention is a polymer having no water-absorbing properties. Its solubility in water (at 25° C.) is 10% or less, more preferably 1% or less, and most preferably 0.1% or less.

A hydrophobic monomer which forms a hydrophobic polymer can be selected from vinyl esters, acrylic esters, methacrylic esters, olefins, styrenes, crotonic esters, itaconic diesters, maleic diesters, fumaric diesters, allyl compounds, vinyl ethers, vinyl ketones, or the like. The hydrophobic polymer may be either a homopolymer consisting of one type of monomer, or copolymer consisting of two or more types of monomers.

Examples of a hydrophobic polymer that is preferably used in the present invention may include polystyrene, polyethylene, polypropylene, polyethylene terephthalate, polyvinyl chloride, polymethyl methacrylate, polyester, and nylon.

A substrate is coated with a hydrophobic polymer according to common methods. Examples of such a coating method may include spin coating, air knife coating, bar coating, blade coating, slide coating, curtain coating, spray method, evaporation method, cast method, and dip method.

In the dip method, coating is carried out by contacting a substrate with a solution of a hydrophobic polymer, and then with a liquid which does not contain the hydrophobic polymer. Preferably, the solvent of the solution of a hydrophobic polymer is the same as that of the liquid which does not contain said hydrophobic polymer.

In the dip method, a layer of a hydrophobic polymer having an uniform coating thickness can be obtained on a surface of a substrate regardless of inequalities, curvature and shape of the substrate by suitably selecting a coating solvent for hydrophobic polymer.

The type of coating solvent used in the dip method is not particularly limited, and any solvent can be used so long as it can dissolve a part of a hydrophobic polymer. Examples thereof include formamide solvents such as N,N-dimethylformamide, nitrile solvents such as acetonitrile, alcohol solvents such as phenoxyethanol, ketone solvents such as 2-butanone, and benzene solvents such as toluene, but are not limited thereto.

In the solution of a hydrophobic polymer which is contacted with a substrate, the hydrophobic polymer may be dissolved completely, or alternatively, the solution may be a suspension which contains undissolved component of the hydrophobic polymer. The temperature of the solution is not particularly limited, so long as the state of the solution allows a part of the hydrophobic polymer to be dissolved. The temperature is preferably −20° C. to 100° C. The temperature of the solution may be changed during the period when the substrate is contacted with a solution of a hydrophobic polymer. The concentration of the hydrophobic polymer in the solution is not particularly limited, and is preferably 0.01% to 30%, and more preferably 0.1% to 10%.

The period for contacting the solid substrate with a solution of a hydrophobic polymer is not particularly limited, and is preferably 1 second to 24 hours, and more preferably 3 seconds to 1 hour.

As the liquid which does not contain the hydrophobic polymer, it is preferred that the difference between the SP value (unit: $(J/cm^3)^{1/2}$) of the solvent itself and the SP value of the hydrophobic polymer is 1 to 20, and more preferably 3 to 15. The SP value is represented by a square root of intermolecular cohesive energy density, and is referred to as solubility parameter. In the present invention, the SP value δ was calculated by the following formula. As the cohesive energy (Ecoh) of each functional group and the mol volume (V), those defined by Fedors were used (R. F. Fedors Polym. Eng. Sci., 14(2), P147, P472(1974)).

$$\delta = (\Sigma Ecoh/\Sigma V)^{1/2}$$

Examples of the SP values of the hydrophobic polymers and the solvents are shown below;
Solvent: 2-phenoxyethanol:25.3 against polymethylmethacrylate-polystyrene copolymer (1:1):21.0
Solvent: acetonitrile:22.9 against polymethylmethacrylate: 20.3
Solvent: toluene:18.7 against polystyrene:21.6

The period for contacting a substrate with a liquid which does not contain the hydrophobic polymer is not particularly limited, and is preferably 1 second to 24 hours, and more preferably 3 seconds to 1 hour. The temperature of the liquid is not particularly limited, so long as the solvent is in a liquid state, and is preferably −20° C. to 100° C. The temperature of the liquid may be changed during the period when the substrate is contacted with the solvent. When a less volatile solvent is used, the less volatile solvent may be substituted with a volatile solvent which can be dissolved in each other after the substrate is contacted with the less volatile solvent, for the purpose of removing the less volatile solvent.

The coating thickness of a hydrophobic polymer is not particularly limited, but it is preferably between 0.1 nm and 500 nm, and particularly preferably between 1 nm and 300 nm.

Examples of a polyhydroxy polymer used in the present invention may include polysaccharides (e.g. agarose gel, dextran, carrageenan, alginic acid, starch, and cellulose), and synthetic polymers (e.g. polyvinyl alcohol). In the present invention, polysaccharides are preferably used, and dextran is most preferable.

In the present invention, a polyhydroxy polymer having a mean molecular weight between 10,000 and 2,000,000 is preferably used. A polyhydroxy polymer having a mean molecular weight preferably between 20,000 and 2,000,000, more preferably between 30,000 and 1,000,000, and most preferably between 200,000 and 800,000, can be used.

For example, a polyhydroxy polymer is allowed to react with bromoacetic acid under basic conditions, so that it can be carboxylated. By controlling reaction conditions, a certain ratio of hydroxy groups contained in a polyhydroxy compound at an initial stage can be carboxylated. In the present invention, 1% to 90% hydroxy groups can be carboxylated, for example. The carboxylation rate of a surface coated with any given polyhydroxy polymer can be calculated by the following method. Using a di-tert-butylcarbodiimide/pyridine catalyst, the surface of a film is subjected to gas phase modification with trifluoroethanol at 50° C. for 16 hours. Thereafter, the amount of fluorine derived from trifluoroethanol is measured by ESCA (electron spectroscopy for chemical analysis), and the ratio between the amount of fluorine and the amount of oxygen on the film surface (hereinafter referred to as F/O value) is calculated. A theoretical F/O value obtained when all hydroxy groups have been carboxylated is set at 100%. Then, a F/O value obtained by carboxylation under certain conditions is measured. Thus, a carboxylation rate at that time can be calculated.

A polyhydroxy polymer can be attached to a metal film via an organic molecule $X^1$—$R^1$—$Y^1$. Such an organic molecule $X^1$—$R^1$—$Y^1$ will be described in detail.

$X^1$ is a group having ability to bind to a metal film. Specifically, asymmetrical or symmetrical sulfide (—$SSR^{11}Y^{11}$, —$SSR^1Y^1$), sulfide (—$SR^{11}Y^{11}$, —$SR^1Y^1$), diselenide (—$SeSeR^{11}Y^{11}$, —$SeSeR^1Y^1$), selenide (—$SeR^{11}Y^{11}$, —$SeR^1Y^1$), thiol (—SH), nitrile (—CN), isonitrile, nitro (—$NO_2$), selenol (—SeH), a trivalent phosphorus compound, isothiocyanate, xanthate, thiocarbamate, phosphine, thioacid, and dithioacid (—COSH, —CSSH) are preferably used.

$R^1$ (and $R^{11}$) are discontinued by hetero atoms in some cases. For a moderately dense load, these are preferably straight chains (that are not branched), and these are hydrocarbon chains containing double and/or triple bonds in some cases. Such a chain preferably has a length consisting of more than 10 atoms. A carbon chain may be perfluorinated in some cases.

$Y^1$ and $Y^{11}$ are groups for allowing a polyhydroxy polymer to bind with a metal film. $Y^1$ and $Y^{11}$ are preferably identical and have properties of capable of binding to a polyhydroxy polymer directly or after activation. Specifically, a hydroxyl, carboxyl, amino, aldehyde, hydrazide, carbonyl, epoxy, or vinyl group can be used.

Specific examples of an organic molecule $X^1$—$R^1$—$Y^1$ used herein may include 10-carboxy-1-decanethiol, 4,4'-dithiodibutyric acid, 11-hydroxy-1-undecanethiol, and 11-amino-1-undecanethiol.

A sulfur compound such as thiol or disulfide spontaneously adsorbs on a precious metal substrate such as gold, so as to provide an ultra-thin membrane with a size of a single molecule. In addition, since an aggregate thereof has a sequence that depends on the crystal lattice of a substrate or the molecular structure of an admolecule, it is called a self assembled membrane. In the present invention, 7-carboxy-1-heptanethiol, 10-carboxy-1-decanethiol, 4,4'-dithiodibutyric acid, 11-hydroxy-1-undecanethiol, 11-amino-1-undecanethiol, or the like can be used as such a self assembled membrane.

A substrate used in the present invention may further have a linker for allowing the compound represented by the formula (A) to bind to the substrate.

A specific example of a linker used in the present invention is a compound represented by the following formula (4):

$$X^{20}\text{-}L^{20}\text{-}Y^{20} \qquad (4)$$

wherein $X^{20}$ represents a group capable of reacting with a hydrophobic polymer, a polyhydroxy polymer, or a functional group contained in a self assembled membrane; $L^{20}$ represents a divalent linking group; and $Y^{20}$ represents a group capable of reacting with a compound represented by the formula (A), so as to form a covalent bond.

In formula (4), $X^{20}$ represents a group capable of reacting with a hydrophobic polymer, a polyhydroxy polymer, or a functional group contained in a self assembled membrane. Preferred examples may include a halogen atom, an amino group, an amino group protected by a protecting group, a carboxyl group, a carbonyl group having a leaving group, a hydroxyl group, a hydroxyl group protected by a protecting group, an aldehyde group, —$NHNH_2$, —$N\!=\!C\!=\!O$, —$N\!=\!C\!=\!S$, an epoxy group, and a vinyl group.

The term "protecting group" is used herein to mean a group capable of deprotecting a target group in a reaction system, so as to allow it to form a functional group. Examples of a protecting group for an amino group may include a tert-butyloxycarbonyl group (Boc), a 9-fluorenyl-methyloxycarbonyl group (Fmoc), a nitrophenylsulphenyl group (Nps), and a dithiasuccinyl group (Dts).

In addition, an acyl group may be an example of a protecting group for a hydroxyl group.

Examples of a leaving group used herein may include a halogen atom, an alkoxy group, an aryloxy group, an alkylcarbonyloxy group, an arylcarbonyloxy group, a halogenated alkylcarbonyloxy group, an alkylsulfonyloxy group, a halogenated alkylsulfonyloxy group, and an arylsulfonyloxy group.

Moreover, an ester group generated as a result of the combination of carboxylic acid, a known dehydrating condensing reagent (e.g. carbodiimide), and an N-hydroxy compound, is also preferably used as a leaving group.

In formula (4), $L^{20}$ represents a divalent linking group. The total number of atoms contained in L is preferably between 2 and 1,000. Preferred examples of $L^{20}$ may include a substituted or unsubstituted alkyl group, a substituted or unsubstituted alkyleneoxy group, a substituted or unsubstituted aryleneoxy group, and a divalent linking group formed by binding $X^{20}$ in formula (4) to another molecule $Y^{20}$ and continuously repeating such a structure.

In formula (4), $Y^{20}$ represents a group capable of reacting with the compound represented by the formula (A), so as to form a covalent bond. Preferred examples of $Y^{20}$ may include a halogen atom, an amino group, an amino group protected by a protecting group, a carboxyl group, a carbonyl group having a leaving group, a hydroxyl group, a hydroxyl group protected by a protecting group, an aldehyde group, —$NHNH_2$, —$N\!=\!C\!=\!O$, —$N\!=\!C\!=\!S$, an epoxy group, and a vinyl group.

As a protecting group and a leaving group, the same above groups may be used.

Specific examples of the compound represented by formula (4) will be given below. However, compounds represented by formula (4) used in the present invention are not limited to such examples.

R-11

It is preferable that the biosensor of the present invention has a functional group capable of immobilizing a physiologically active substance on the outermost surface of the substrate. The term "the outermost surface of the substrate" is used herein to mean "the surface, which is farthest from the substrate," and more specifically, it means "the surface, which is farthest from the surface in a hydrophobic polymer applied on a substrate."

The thus obtained substrate for sensor can immobilize a physiologically active substance on a metal surface or metal film by covalently binding a physiologically active substance via a functional group Y in the aforementioned formula (A).

A physiologically active substance immobilized on the biosensor of the present invention is not particularly limited, as long as it interacts with a measurement target and has any physiological activity. Examples of such a substance may include an immune protein, an enzyme, a microorganism, nucleic acid, a low molecular weight organic compound, a nonimmune protein, an immunoglobulin-binding protein, a sugar-binding protein, a sugar chain recognizing sugar, fatty acid or fatty acid ester, and polypeptide or oligopeptide having a ligand-binding ability. Among them, a protein is preferred, and an enzyme is particularly preferred.

Examples of an immune protein may include an antibody whose antigen is a measurement target, and a hapten. Examples of such an antibody may include various immunoglobulins such as IgG, IgM, IgA, IgE or IgD. More specifically, when a measurement target is human serum albumin, an anti-human serum albumin antibody can be used as an antibody. When an antigen is an agricultural chemical, pesticide, methicillin-resistant *Staphylococcus aureus*, antibiotic, narcotic drug, cocaine, heroin, crack or the like, there can be used, for example, an anti-atrazine antibody, anti-kanamycin antibody, anti-metamphetamine antibody, or antibodies against O antigens 26, 86, 55, 111 and 157 among enteropathogenic *Escherichia coli*.

An enzyme is not particularly limited, as long as it exhibits an activity to a measurement target or substance metabolized from the measurement target. Various enzymes such as oxidoreductase, hydrolase, isomerase, lyase or synthetase can be used. More specifically, when a measurement target is glucose, glucose oxidase is used, and when a measurement target is cholesterol, cholesterol oxidase is used. Moreover, when a measurement target is an agricultural chemical, pesticide, methicillin-resistant *Staphylococcus aureus*, antibiotic, narcotic drug, cocaine, heroin, crack or the like, enzymes such as acetylcholine esterase, catecholamine esterase, noradrenalin esterase or dopamine esterase, which show a specific reaction with a substance metabolized from the above measurement target, can be used.

A microorganism is not particularly limited, and various microorganisms such as *Escherichia coli* can be used.

As nucleic acid, those complementarily hybridizing with nucleic acid as a measurement target can be used. Either DNA (including cDNA) or RNA can be used as nucleic acid. The type of DNA is not particularly limited, and any of native DNA, recombinant DNA produced by gene recombination and chemically synthesized DNA may be used.

As a low molecular weight organic compound, any given compound that can be synthesized by a common method of synthesizing an organic compound can be used.

A nonimmune protein used herein is not particularly limited, and examples of such a nonimmune protein may include avidin (streptoavidin), biotin, and a receptor.

Examples of an immunoglobulin-binding protein used herein may include protein A, protein G, and a rheumatoid factor (RF).

As a sugar-binding protein, for example, lectin is used.

Examples of fatty acid or fatty acid ester may include stearic acid, arachidic acid, behenic acid, ethyl stearate, ethyl arachidate, and ethyl behenate.

A biosensor to which a physiologically active substance is immobilized as described above can be used to detect and/or measure a substance which interacts with the physiologically active substance.

Preferably in the present invention, 1 to 10 molecules of test substances can be bound to a single molecule of physiologically active substance.

In the present invention, it is preferable to detect and/or measure an interaction between a physiologically active substance immobilized on the substrate for sensor and a test substance by a nonelectric chemical method. Examples of a non-electrochemical method may include a surface plasmon resonance (SPR) measurement technique, a quartz crystal microbalance (QCM) measurement technique, and a measurement technique that uses functional surfaces ranging from gold colloid particles to ultra-fine particles.

In a preferred embodiment of the present invention, the biosensor can be used as a biosensor for surface plasmon resonance which is characterized in that it comprises a metal film placed on a transparent substrate.

A biosensor for surface plasmon resonance is a biosensor used for a surface plasmon resonance biosensor, meaning a member comprising a portion for transmitting and reflecting light emitted from the sensor and a portion for immobilizing a physiologically active substance. It may be fixed to the main body of the sensor or may be detachable.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light.

A device using a system known as the Kretschmann configuration is an example of a surface plasmon measurement device for analyzing the properties of a substance to be measured using a phenomenon whereby a surface plasmon is excited with a lightwave (for example, Japanese Patent Laid-Open No. 6-167443). The surface plasmon measurement device using the above system basically comprises a dielectric block formed in a prism state, a metal film that is formed on a face of the dielectric block and comes into contact with a measured substance such as a sample solution, a light source for generating a light beam, an optical system for allowing the above light beam to enter the dielectric block at various angles so that total reflection conditions can be obtained at the interface between the dielectric block and the metal film, and a light-detecting means for detecting the state of surface plasmon resonance, that is, the state of attenuated total reflection, by measuring the intensity of the light beam totally reflected at the above interface.

In order to achieve various incident angles as described above, a relatively thin light beam may be caused to enter the above interface while changing an incident angle. Otherwise, a relatively thick light beam may be caused to enter the above interface in a state of convergent light or divergent light, so that the light beam contains components that have entered therein at various angles. In the former case, the light beam whose reflection angle changes depending on the change of the incident angle of the entered light beam can be detected with a small photodetector moving in synchronization with the change of the above reflection angle, or it can also be detected with an area sensor extending along the direction in which the reflection angle is changed. In the latter case, the light beam can be detected with an area sensor extending to a direction capable of receiving all the light beams reflected at various reflection angles.

With regard to a surface plasmon measurement device with the above structure, if a light beam is allowed to enter the metal film at a specific incident angle greater than or equal to a total reflection angle, then an evanescent wave having an electric distribution appears in a measured substance that is in contact with the metal film, and a surface plasmon is excited by this evanescent wave at the interface between the metal film and the measured substance. When the wave vector of the evanescent light is the same as that of a surface plasmon and thus their wave numbers match, they are in a resonance state, and light energy transfers to the surface plasmon. Accordingly, the intensity of totally reflected light is sharply decreased at the interface between the dielectric block and the metal film. This decrease in light intensity is generally detected as a dark line by the above light-detecting means. The above resonance takes place only when the incident beam is p-polarized light. Accordingly, it is necessary to set the light beam in advance such that it enters as p-polarized light.

If the wave number of a surface plasmon is determined from an incident angle causing the attenuated total reflection (ATR), that is, an attenuated total reflection angle ($\theta SP$), the dielectric constant of a measured substance can be determined. As described in Japanese Patent Laid-Open No. 11-326194, a light-detecting means in the form of an array is considered to be used for the above type of surface plasmon measurement device in order to measure the attenuated total reflection angle ($\theta SP$) with high precision and in a large dynamic range. This light-detecting means comprises multiple photo acceptance units that are arranged in a certain direction, that is, a direction in which different photo acceptance units receive the components of light beams that are totally reflected at various reflection angles at the above interface.

In the above case, there is established a differentiating means for differentiating a photodetection signal outputted from each photo acceptance unit in the above array-form light-detecting means with regard to the direction in which the photo acceptance unit is arranged. An attenuated total reflection angle ($\theta SP$) is then specified based on the derivative value outputted from the differentiating means, so that properties associated with the refractive index of a measured substance are determined in many cases.

In addition, a leaking mode measurement device described in "Bunko Kenkyu (Spectral Studies)" Vol. 47, No. 1 (1998), pp. 21 to 23 and 26 to 27 has also been known as an example of measurement devices similar to the above-described device using attenuated total reflection (ATR). This leaking mode measurement device basically comprises a dielectric block formed in a prism state, a clad layer that is formed on a face of the dielectric block, a light wave guide layer that is formed on the clad layer and comes into contact with a sample solution, a light source for generating a light beam, an optical system for allowing the above light beam to enter the dielectric block at various angles so that total reflection conditions can be obtained at the interface between the dielectric block and the clad layer, and a light-detecting means for detecting the excitation state of waveguide mode, that is, the state of attenuated total reflection, by measuring the intensity of the light beam totally reflected at the above interface.

In the leaking mode measurement device with the above structure, if a light beam is caused to enter the clad layer via the dielectric block at an incident angle greater than or equal to a total reflection angle, only light having a specific wave number that has entered at a specific incident angle is transmitted in a waveguide mode into the light wave guide layer, after the light beam has penetrated the clad layer. Thus, when the waveguide mode is excited, almost all forms of incident light are taken into the light wave guide layer, and thereby the state of attenuated total reflection occurs, in which the intensity of the totally reflected light is sharply decreased at the above interface. Since the wave number of a waveguide light depends on the refractive index of a measured substance placed on the light wave guide layer, the refractive index of the measurement substance or the properties of the measured substance associated therewith can be analyzed by determining the above specific incident angle causing the attenuated total reflection.

In this leaking mode measurement device also, the above-described array-form light-detecting means can be used to detect the position of a dark line generated in a reflected light due to attenuated total reflection. In addition, the above-described differentiating means can also be applied in combination with the above means.

The above-described surface plasmon measurement device or leaking mode measurement device may be used in random screening to discover a specific substance binding to a desired sensing substance in the field of research for development of new drugs or the like. In this case, a sensing substance is immobilized as the above-described measured substance on the above thin film layer (which is a metal film in the case of a surface plasmon measurement device, and is a clad layer and a light guide wave layer in the case of a leaking mode measurement device), and a sample solution obtained by dissolving various types of test substance in a solvent is added to the sensing substance. Thereafter, the above-described attenuated total reflection angle ($\theta SP$) is measured periodically when a certain period of time has elapsed.

If the test substance contained in the sample solution is bound to the sensing substance, the refractive index of the sensing substance is changed by this binding over time. Accordingly, the above attenuated total reflection angle ($\theta SP$) is measured periodically after the elapse of a certain time, and it is determined whether or not a change has occurred in the above attenuated total reflection angle ($\theta SP$), so that a binding state between the test substance and the sensing substance is measured. Based on the results, it can be determined whether or not the test substance is a specific substance binding to the sensing substance. Examples of such a combination between a specific substance and a sensing substance may include an antigen and an antibody, and an antibody and an antibody. More specifically, a rabbit anti-human IgG antibody is immobilized as a sensing substance on the surface of a thin film layer, and a human IgG antibody is used as a specific substance.

It is to be noted that in order to measure a binding state between a test substance and a sensing substance, it is not always necessary to detect the angle itself of an attenuated total reflection angle ($\theta SP$). For example, a sample solution may be added to a sensing substance, and the amount of an attenuated total reflection angle ($\theta SP$) changed thereby may be measured, so that the binding state can be measured based on the magnitude by which the angle has changed. When the above-described array-form light-detecting means and differentiating means are applied to a measurement device using attenuated total reflection, the amount by which a derivative value has changed reflects the amount by which the attenuated total reflection angle (θSP) has changed. Accordingly, based on the amount by which the derivative value has changed, a binding state between a sensing substance and a test substance can be measured (Japanese Patent Application No. 2000-398309 filed by the present applicant). In a measuring method and a measurement device using such attenuated total reflection, a sample solution consisting of a solvent and a test substance is added dropwise to a cup- or petri dish-shaped measurement chip wherein a sensing substance is immobilized on a thin film layer previously formed at the bottom, and then, the above-described amount by which an attenuated total reflection angle (θSP) has changed is measured.

Moreover, Japanese Patent Laid-Open No. 2001-330560 describes a measurement device using attenuated total reflection, which involves successively measuring multiple measurement chips mounted on a turntable or the like, so as to measure many samples in a short time.

When the biosensor used in the present invention is used in surface plasmon resonance analysis, it can be applied as a part of various surface plasmon measurement devices described above.

Furthermore, in the measurement method of the present invention, a substance interacting with a physiologically active substance is detected or measured by methods such as the aforementioned surface plasmon resonance analysis, and simultaneously or thereafter, the biological activity of the above physiologically active substance is measured on the same biosensor.

The term "biological activity" used in the present invention includes enzyme activity, antibody activity, receptor activity, metabolism activity, membrane potential, ion emission level, and gene expression level.

The term "enzyme" is a genetic name of proteins having catalytic action, which smoothly promotes various chemical reactions occurring in a body, such as food digestion. The term "catalyst" generally means a substance acting as an intermediary to carry out chemical reactions efficiently.

The measurement principle of enzyme activity is described in *Tanpakushitsu, Koso no Kiso Jikken Ho* (Basic experiment methods for proteins and enzymes), Takeichi Horio, Jinpei Yamashita, Chapter IV. Examples of a detection method may include: (1) spectroscopic measurement method; (2) fluorescence method; (3) electrode method; and (4) luminescence method. In addition, the method described in *Shin-seikagaku jikken koza, tanpakushitsu V, Koso meneki sokutei ho, 3$^{rd}$ edition, Enzyme Immunoassay, Seikagaku jikken ho* (New Biochemical Experiment Course, Protein V, Enzyme Immunoassay, 3$^{rd}$ edition, Enzyme Immunoassay, Biochemical Experimental Methods), can also be applied, for example.

When enzyme activity is measured by the fluorescence method for example, a substrate specific to an enzyme (a substrate, only products decomposed with the enzyme of which emit fluorescence) is allowed to react therewith, and fluorescence in the decomposed products is measured, so as to measure enzyme activity.

When enzyme activity is measured by the spectroscopic measurement method, a difference in spectroscopic properties existing between a substrate and a product is used. A temporal change thereof is measured, and the initial speed of the enzyme reaction is thereby obtained, so as to measure enzyme activity.

When enzyme activity is measured by the electrode method, a method using an automatic titrator is applied. A pH change in a sample solution due to acid or base generated as a result of chemical reactions including enzyme reaction is electrically detected, so as to measure enzyme activity.

When enzyme activity is measured by the luminescence method, an antibody or antigen has been labeled with enzyme. After an antigen-antibody reaction, a chemoluminescent substrate specific to the enzyme (a substrate, only products decomposed with the enzyme of which emit chemoluminescence) is allowed to react therewith, and chemoluminescence in the decomposed products is measured, so as to measure enzyme activity.

When antibody activity is measured, an antigen of interest is allowed to bind to the inner wall of each hole of a plastic plate used for ELISA, and a test sample containing an antibody to be measured is then added thereto for reaction. The antibody binds to the antigen as a solid phase. The larger the amount of the antibody contained in the test sample, the higher the binding amount that can be obtained. Thereafter, an anti-immunoglobulin antibody that has been labeled with enzyme is further added thereto. The labeled antibody binds to the above antibody binding to the solid phase. The larger the amount of the above antibody, the higher the binding amount of the labeled antibody that can be obtained. An unreacted labeled antibody portion is removed, and a substrate that emits light as a result of the action of the enzyme is then added thereto. Such a substrate emits light depending on the amount of enzyme. Thus, the larger the amount of the enzyme-labeled antibody binding to a substrate, the stronger the color tone that is emitted by the substrate. The amount of the antibody contained in the test sample can be obtained by measuring the intensity of the color of the solution with a colorimeter. If a known amount of antibody is diluted stepwise and the amount of each diluted antibody is then measured, the amount of an antibody contained in a test sample can be quantified by comparison with the above obtained values.

When receptor activity is measured, one or more receptors or ligands immobilized on a supporting medium are allowed to come into contact with an analyte containing a ligand or receptor that has been labeled with an antigen. Thereafter, the antigen-labeled ligand or receptor binding to one or more receptors or ligands immobilized on the supporting medium is allowed to come into contact with an antibody reacting with the above antigen (for example, an antibody labeled with enzyme used for detection), so as to carry out an antigen-antibody reaction. Thus, the presence of the antibody bound is detected, thereby detecting a ligand or receptor contained in the analyte.

A metabolism activity level, a membrane potential, an ion emission level, and a gene expression level are all measured by known methods.

The present invention will be further specifically described in the following examples. However, the examples are not intended to limit the scope of the present invention.

EXAMPLES (1) Surface Plasmon Resonance Measurement Device and Dielectric Block

Figure 1:
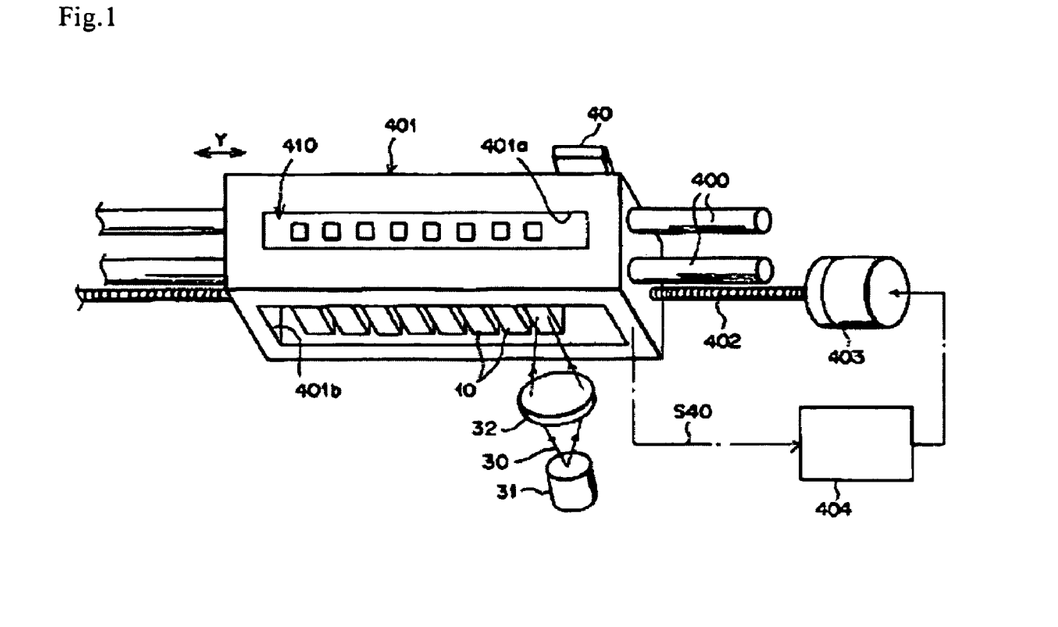
FIG. 1 shows the plasmon resonance measurement device.
Figure 2:
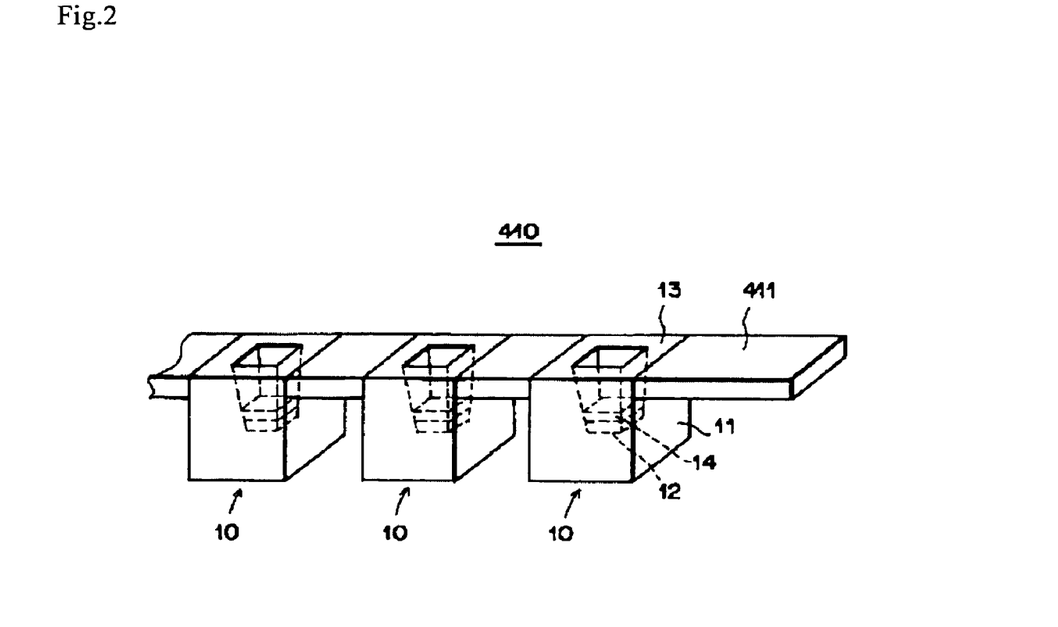
FIG. 2 shows the dielectric block.

The experiments described below were carried out using the device shown in FIG. 22 of Japanese Patent Laid-Open No. 2001-330560 (hereinafter referred to as the surface plasmon resonance measurement device of the present invention), which is shown in FIG. 1 of the present specification, and also using the dielectric block shown in FIG. 23 of the same above publication (hereinafter referred to as the dielectric block of the present invention), which is shown in FIG. 2 of the present specification.

The surface plasmon resonance measurement device shown in FIG. 1 comprises, as a supporting medium for supporting a measurement unit, a slide block 401, which engages in a slidable manner with two guide rods 400, 400 that are disposed in parallel with each other, and flexibly linearly moves along them in the direction of arrow Y in the figure. A precision screw 402 disposed in parallel with the above guide rods 400, 400, is threadably mounted on the above slide block 401. This precision screw 402 is corotated or couterrotated by a pulse motor 403 that constitutes a supporting medium-driving means together with the above screw.

It is to be noted that the driving of the pulse motor 403 is controlled by a motor controller 404. That is to say, an output signal S40 of a linear encoder (not shown), which is incorporated into the slide block 401 to detect the position of the above slide block 401 in the longitudinal direction of the guide rods 400, 400, is inputted to the motor controller 404, and the motor controller 404 controls the driving of the pulse motor 403 based on the signal S40.

A laser light source 31, a condenser lens 32, and a photodetector 40 are disposed on the lower side of the guide rods 400, 400, such that the laser light source 31 and condenser lens 32, and the photodetector 40 sandwich the slide block 401 moving along the guide rods. The condenser lens 32 condenses a light beam 30. In addition, the photodetector 40 is established.

In the present embodiment, a stick-form unit connection body 410 formed by connecting and fixing 8 pieces of measurement unit 10 is used, as an example. Such measurement unit 10 is equipped into the slide block 401 in a state where eight units are disposed in line.

FIG. 2 shows the structure of the unit connection body 410 in detail. As shown in the figure, the unit connection body 410 is formed by connecting 8 pieces of the measurement unit 10 by a connecting member 411.

The measurement unit 10 is formed by molding a dielectric block 11 and a sample-retaining frame 13 using a transparent resin, for example. The measurement unit 10 constitutes an exchangeable measurement chip on a turntable. In order to create such an exchangeable measurement chip on such a turntable, the measurement unit 10 may be fitted into a through-hole formed on the turntable, for example. In the present example, a sensing substance 14 is immobilized on a metal membrane 12.

(2) Measurement Chip

In the following experiment, the measurement chip described in Japanese Patent Laid-Open No. 2005-98770 (hydrogel-coated chip) was used. Specifically, a measurement chip coated with hydrogel was produced by the following procedures.

The dielectric block of the present invention, which had been coated with gold via evaporation resulting in a metal membrane with a thickness of 50 nm, was treated with a Model-208 UV-ozone cleaning system (TECHNOVISION INC) for 30 minutes. Thereafter, a solution of 5.0 mM 11-hydroxy-1-undecanethiol in ethanol/water (80/20) was added thereto, such that the solution was allowed to come into contact with the metal membrane. Thus, a surface treatment was carried out at 25° C. for 18 hours. Thereafter, the resultant product was washed with ethanol 5 times, with a mixed solvent consisting of ethanol and water once, and then with water 5 times.

Subsequently, 10% by weight of epichlorohydrin solution (solvent: a mixed solution of 0.4 M sodium hydroxide and diethylene glycol dimethyl ether at a ratio of 1:1) was allowed to come into contact with the surface coated with 11-hydroxy-1-undecanethiol, and the reaction was carried out in a shaking incubator at 25° C. for 4 hours. Thereafter, the surface was washed with ethanol twice and then with water 5 times. Subsequently, 4.5 ml of 1 M sodium hydroxide was added to 40.5 ml of 25%-by-weight dextran (T500, Pharmacia) aqueous solution, and the thus obtained solution was then allowed to come into contact with the epichlorohydrin-treated surface. Thereafter, the resultant product was incubated in a shaking incubator at 25° C. for 20 hours. The surface was then washed with water at 50° C. 10 times. Subsequently, a mixture obtained by dissolving 3.5 g of bromoacetic acid in 27 g of a 2 M sodium hydroxide solution was allowed to come into contact with the aforementioned dextran-treated surface, and the resultant product was incubated in a shaking incubator at 28° C. for 16 hours. The surface was washed with water, and the aforementioned procedure was repeated once again. The thus obtained sample was defined as a hydrogel-coated measurement chip.

Also, a chip used for biosensor that was coated with a hydrophobic polymer (PMMA measurement chip) was produced as follows.

(i) Production of Chip used for Biosensor Coated with Polymethyl Methacrylate

A cover glass with a size of 1 cm×1 cm, which had been coated with gold via evaporation resulting in a gold membrane with a thickness of 500 angstroms, was treated with a Model-208 UV-ozone cleaning system (TECHNOVISION INC.) for 30 minutes. Thereafter, it was placed in a spin coater (MODEL ASS-303; manufactured by ABLE) and then rotated at 1,000 rpm. 50 μl of a methyl ethyl ketone solution containing polymethyl methacrylate (2 mg/ml) was added dropwise to the center of the cover glass coated with gold via evaporation, and 2 minutes later, the rotation was terminated. The thickness of the membrane was measured by the ellipsometry method (In-Situ Ellipsometer MAUS-101; manufactured by Five Lab). As a result, the thickness of the polymethyl methacrylate membrane was found to be 200 angstroms. This sample is called a PMMA surface chip.

(ii) Introduction of COOH Group into PMMA Surface

The cover glass coated with polymethyl methacrylate as described above was immersed in an NaOH aqueous solution (1 N) at 40° C. for 16 hours, followed by washing with water 3 times. This sample is called a PMMA/COOH surface chip.

(iii) Production of Surface having Linker

The PMMA/COOH surface chip as produced in (ii) above was immersed in 2 ml of a mixed solution consisting of 1-ethyl-2,3-dimethylaminopropylcarbodiimide (400 mM) and N-hydroxysuccinimide (100 mM) for 60 minutes. Thereafter, it was immersed in 2 ml of an α-amino-polyethyleneoxy-ω-carboxylic acid (mean molecular weight: 5,000) aqueous solution (10 mM) for 16 hours. The resultant product was finally washed with water 5 times. This sample is called a PMMA/PEO-C surface chip.

Example 1

Measurement of Trypsin and Leupeptin

Trypsin (manufactured by Worthington) was immobilized on a measurement chip. Interaction measurement was carried out using a surface plasmon resonance measurement device.

(1) Immobilization of Trypsin

A mixed solution consisting of 1-ethyl-2,3-dimethylaminopropylcarbodiimide (400 mM) and N-hydroxysuccinimide (100 mM) was added to a hydrogel-coated chip, followed by leaving at rest for 20 minute. Thereafter, the resultant product was washed with an HBS-N buffer containing 10 mM $CaCl_2$. Subsequently, trypsin (1 mg/ml, 10 mM $CaCl_2$-containing HBS-N buffer) was added thereto, followed by leaving at rest for 30 minutes. Thereafter, the resultant product was washed with a 10 mM $CaCl_2$-containing HBS-N buffer. The used HBS-N buffer is composed of 0.01 mol/l (pH 7.4) HEPES (N-2-hydroxyethylpiperazine-N'-2-ethanesulfonic acid) and 0.15 mol/l NaCl.

Thereafter, an ethanolamine/HCl solution (1M, pH 8.5) was added to the measurement chip, followed by washing with an HBS-N buffer (manufactured by Biacore), so as to block COOH groups that remained without reacting with trypsin.

By the aforementioned operations, trypsin was immobilized on the surface of the measurement chip via a covalent bond. The amount by which resonance signals (RU value) obtained before the addition of trypsin and after washing it had changed was defined as the immobilized amount of trypsin (RU value). The amount by which resonance signals had changed due to immobilization of trypsin was found to be 1,360 RU.

(2) Detection of Substance Interacting with Physiologically Active Substance

A measurement chip was washed with an HBS-N buffer. Thereafter, the measurement chip was equipped into a surface plasmon resonance measurement device, and a leupeptin solution (0.002 mM, HBS-N buffer) was added thereto, followed by leaving at rest for 10 minutes. The amount by which resonance signals (RU value) had changed was defined as the amount of leupeptin (manufactured by ICN) binding to trypsin.

(3) Measurement of Biological Activity of Physiologically Active Substance

Using the chip after the measurement of the amount of leupeptin binding to trypsin described in (2) above, the enzyme activity of trypsin was measured. Specifically, a substrate specific to trypsin (benzoyl-L-arginine-4-methylcoumarin-7-amide (hereinafter referred to as Bz-Arg-MCA); Peptide Institute, Inc.) was allowed to react with trypsin, and fluorescence in the decomposed product was measured.

(4) Reaction of Bz-Arg-MCA

The HBS-N buffer contained in the measurement chip was removed, and a leupeptin solution (0.002 mM, HBS-N buffer) and 0.1 mM Bz-Arg-MCA were added thereto. The reaction was then carried out for 10, 30, 60, and 120 minutes.

(5) Fluorescence Measurement

Fluorescence measurement was carried out regarding the reaction for each of the aforementioned reaction times, using the BMGLabTechnologies FLUOstar measurement device (excitation: 380 nm; and emission: 460 nm).

Example 2

Measurement of Trypsin and Nitrofurantoin

Trypsin (manufactured by Worthington) was immobilized on a measurement chip. Interaction measurement was carried out using a surface plasmon resonance measurement device.

(1) Immobilization of Trypsin

A mixed solution of 1-ethyl-2,3-dimethylaminopropylcarbodiimide (400 mM) and N-hydroxysuccinimide (100 mM) was added to a hydrogel-coated chip, followed by leaving at rest for 20 minute. Thereafter, the resultant product was washed with an HBS-N buffer containing 10 mM $CaCl_2$. Subsequently, trypsin (1 mg/ml, 10 mM $CaCl_2$-containing HBS-N buffer) was added thereto, followed by leaving at rest for 30 minutes. Thereafter, the resultant product was washed with a 10 mM $CaCl_2$-containing HBS-N buffer.

Thereafter, an ethanolamine/HCl solution (1M, pH 8.5) was added to the measurement chip, followed by washing with an HBS-N buffer (manufactured by Biacore), so as to block COOH groups that remained without reacting with trypsin.

By the aforementioned operations, trypsin was immobilized on the surface of the measurement chip via a covalent bond. The amount by which resonance signals (RU value) obtained before the addition of trypsin and after washing it had changed was defined as the immobilized amount of trypsin (RU value). The amount by which resonance signals had changed due to immobilization of trypsin was found to be 1,500 RU.

(2) Detection of Substance Interacting with Physiologically Active Substance

A measurement chip was washed with an HBS-N buffer. Thereafter, the measurement chip was equipped into a surface plasmon resonance measurement device, and a nitrofurantoin solution (manufactured by Sigma; 0.002 mM; HBS-N/DMSO buffer (95:5)) was added thereto, followed by leaving at rest for 10 minutes. The amount by which resonance signals (RU value) had changed was defined as the amount of nitrofurantoin binding to trypsin.

(3) Measurement of Biological Activity of Physiologically Active Substance

Using the chip after the measurement of the amount of nitrofurantoin binding to trypsin in (2) above, the enzyme activity of trypsin was measured. Specifically, a substrate specific to trypsin (benzoyl-L-arginine-4-methylcoumarin-7-amide (hereinafter referred to as Bz-Arg-MCA); Peptide Institute, Inc.) was allowed to react with trypsin, and fluorescence in the decomposed product was measured.

(4) Reaction of Bz-Arg-MCA

The HBS-N/DMSO buffer (95:5) contained in the measurement chip was removed, and a nitrofurantoin solution (0.002 mM, HBS-N buffer) and 0.1 mM Bz-Arg-MCA were added thereto. The reaction was then carried out for 10, 30, 60, and 120 minutes.

(5) Fluorescence Measurement

Fluorescence measurement was carried out regarding the reaction for each of the aforementioned reaction times, using the BMGLabTechnologies FLUstar measurement device (excitation: 380 mm; and emission: 460 nm).

Example 3

Measurement of Trypsin and Chymostatin

Trypsin (manufactured by Worthington) was immobilized on a measurement chip. Interaction measurement was carried out using a surface plasmon resonance measurement device.

(1) Immobilization of Trypsin

A mixed solution of 1-ethyl-2,3-dimethylaminopropylcarbodiimide (400 mM) and N-hydroxysuccinimide (100 mM) was added to a hydrogel-coated chip, followed by leaving at rest for 20 minute. Thereafter, the resultant product was washed with an HBS-N buffer containing 10 mM $CaCl_2$. Subsequently, trypsin (1 mg/ml, 10 mM $CaCl_2$-containing HBS-N buffer) was added thereto, followed by leaving at rest for 30 minutes. Thereafter, the resultant product was washed with a 10 mM $CaCl_2$-containing HBS-N buffer.

Thereafter, an ethanolamine/HCl solution (1M, pH 8.5) was added to the measurement chip, followed by washing with an HBS-N buffer (manufactured by Biacore), so as to block COOH groups that remained without reacting with trypsin.

By the aforementioned operations, trypsin was immobilized on the surface of the measurement chip via a covalent bond. The amount by which resonance signals (RU value) obtained before the addition of trypsin and after washing it had changed was defined as the immobilized amount of trypsin (RU value). The amount by which resonance signals had changed due to immobilization of trypsin was found to be 1,400 RU.

(2) Detection of Substance Interacting with Physiologically Active Substance

A measurement chip was washed with an HBS-N buffer. Thereafter, the measurement chip was equipped into a surface plasmon resonance measurement device, and a chymostatin solution (0.002 mM, HBS-N buffer) was added thereto, followed by leaving at rest for 10 minutes. The amount by which resonance signals (RU value) had changed was defined as the amount of chymostatin (manufactured by ICN) binding to trypsin.

(3) Measurement of Biological Activity of Physiologically Active Substance

Using the chip after the measurement of the amount of chymostatin binding to trypsin in (2) above, the enzyme activity of trypsin was measured. Specifically, a substrate specific to trypsin (benzoyl-L-arginine-4-methylcoumarin-7-amide (hereinafter referred to as Bz-Arg-MCA); Peptide Institute, Inc.) was allowed to react with trypsin, and fluorescence in the decomposed product was measured.

(4) Reaction of Bz-Arg-MCA

The HBS-N buffer contained in the measurement chip was removed, and a chymostatin solution (0.002 mM, HBS-N buffer) and 0.1 mM Bz-Arg-MCA were added thereto. The reaction was then carried out for 10, 30, 60, and 120 minutes.

(5) Fluorescence Measurement

Fluorescence measurement was carried out regarding the reaction for each of the aforementioned reaction times, using the BMGLabTechnologies FLUstar measurement device (excitation: 380 nm; and emission: 460 nm).

Example 4

Measurement of Trypsin and Measurement Buffer

Trypsin (manufactured by Worthington) was immobilized on a measurement chip. Interaction measurement was carried out using a surface plasmon resonance measurement device.

(1) Immobilization of Trypsin

A mixed solution of 1-ethyl-2,3-dimethylaminopropylcarbodiimide (400 mM) and N-hydroxysuccinimide (100 mM) was added to a hydrogel-coated chip, followed by leaving at rest for 20 minute. Thereafter, the resultant product was washed with an HBS-N buffer containing 10 mM $CaCl_2$. Subsequently, trypsin (1 mg/ml, 10 mM $CaCl_2$-containing HBS-N buffer) was added thereto, followed by leaving at rest for 30 minutes. Thereafter, the resultant product was washed with a 10 mM $CaCl_2$-containing HBS-N buffer.

Thereafter, an ethanolamine/HCl solution (1M, pH 8.5) was added to the measurement chip, followed by washing with an HBS-N buffer (manufactured by Biacore), so as to block COOH groups that remained without reacting with trypsin.

By the aforementioned operations, trypsin was immobilized on the surface of the measurement chip via a covalent bond. The amount by which resonance signals (RU value) obtained before the addition of trypsin and after washing it had changed was defined as the immobilized amount of trypsin (RU value). The amount by which resonance signals had changed due to immobilization of trypsin was found to be 1,450 RU.

(2) Detection of Substance Interacting with Physiologically Active Substance

A measurement chip was washed with an HBS-N buffer. Thereafter, the measurement chip was equipped into a surface plasmon resonance measurement device, and an HBS-N buffer was added thereto, followed by leaving at rest for 10 minutes. The amount by which resonance signals (RU value) had changed was defined as the amount of HBS-N buffer binding to trypsin.

(3) Measurement of Biological Activity of Physiologically Active Substance

Using the chip after the measurement of the amount of HBS-N buffer binding to trypsin in (2) above, the enzyme activity of trypsin was measured. Specifically, a substrate specific to trypsin (benzoyl-L-arginine-4-methylcoumarin-7-amide (hereinafter referred to as Bz-Arg-MCA); Peptide Institute, Inc.) was allowed to react with trypsin, and fluorescence in the decomposed product was measured.

(4) Reaction of Bz-Arg-MCA

The HBS-N buffer contained in the measurement chip was removed, and an HBS-N buffer and 0.1 mM Bz-Arg-MCA were added thereto. The reaction was then carried out for 10, 30, 60, and 120 minutes.

(5) Fluorescence Measurement

Fluorescence measurement was carried out regarding the reaction for each of the aforementioned reaction times, using the BMGLabTechnologies FLUstar measurement device (excitation: 380 nm; and emission: 460 nm).

The results of the above-described measurements are shown in the following

TABLE 1

| Substance interacting with Trypsin | Bond of substance interacting with trypsin (RU) | Measurement results of fluorescence intensity (120 minutes) |
|---|---|---|
| None | — | 580 |
| Leupeptin | 22 | 2 |
| Nitrofurantoin | 10 | 570 |
| Chymostatin | 0 | 576 |

In Table 1, the measurement result of a fluorescence intensity in a case where no substances interacted with trypsin indicates the enzyme activity level obtained when no interactive substances act on trypsin. When leupeptin was used, leupeptin bound to the enzyme activity site of trypsin, thereby inhibiting the enzyme activity. When nitrofurantoin was used, nitrofurantoin bound to trypsin, but no inhibitory action on the enzyme activity of trypsin was observed. Thus, it is considered that this is a non-specific bond. When chymostatin was used, this substance did not bind to trypsin, and thus, no inhibitory action on the enzyme activity of trypsin was observed.

The results shown in Table 1 indicate that the measurement method of the present invention enables two types of measurements, a binding reaction and an enzyme reaction, using a small amount of protein, and that it becomes possible to determine whether or not the bound compound has bound to an active site, by measuring the activity of the compound.

Example 5

Measurement of Trypsin and Leupeptin (Measured using PMMA Membrane and Biacore 3000)

Trypsin (manufactured by Worthington) was immobilized on a PMMA measurement chip. Interaction measurement was carried out using a surface plasmon resonance measurement device (Biacore 3000).

(1) Immobilization of Trypsin

A PMMA measurement chip was equipped into Biacore 3000. A mixed solution of 1-ethyl-2,3-dimethylaminopropylcarbodiimide (400 mM) and N-hydroxysulfosuccinimide (100 mM) was added thereto, followed by reaction for 7 minutes. Thereafter, trypsin (0.05 mg/ml, 10 mM CaCl$_2$-containing HBS-N buffer) was added thereto, followed by reaction for 7 minutes.

Thereafter, an ethanolamine/HCl solution (1M, pH 8.5) was added to the measurement chip, followed by reaction for 7 minutes, so as to block COOH groups that remained without reacting with trypsin.

By the aforementioned operations, trypsin was immobilized on the surface of the PMMA measurement chip via a covalent bond. The amount by which resonance signals (RU value) obtained before the addition of trypsin and after washing it had changed was defined as the immobilized amount of trypsin (RU value). The amount by which resonance signals had changed due to immobilization of trypsin was found to be 2,000 RU.

(2) Detection of Substance Interacting with Physiologically Active Substance

A leupeptin solution (0.002 mM, HBS-N buffer) was added to a measurement chip, followed by reaction for 10 minutes. The amount by which resonance signals (RU value) had changed was defined as the amount of leupeptin (manufactured by ICN) binding to trypsin.

(3) Measurement of Biological Activity of Physiologically Active Substance

Using the PMMA chip after the measurement of the amount of leupeptin binding to trypsin in (2) above, the enzyme activity of trypsin was measured. Specifically, a substrate specific to trypsin (benzoyl-L-arginine-4-methylcoumarin-7-amide (hereinafter referred to as Bz-Arg-MCA); Peptide Institute, Inc.) was allowed to react with trypsin, and fluorescence in the decomposed product was measured.

(4) Reaction of Bz-Arg-MCA

The inside of the PMMA measurement chip was washed with an HBS-N buffer. Thereafter, a leupeptin solution (0.002 mM, HBS-N buffer) and 0.1 mM Bz-Arg-MCA were added thereto. The reaction was then carried out for 10, 30, 60, and 120 minutes.

(5) Fluorescence Measurement

Fluorescence measurement was carried out regarding the reaction for each of the aforementioned reaction times, using the BMGLabTechnologies FLUstar measurement device (excitation: 380 nm; and emission: 460 nm).

(6) Measurement Results

The obtained results were equivalent to the values obtained with CM5 cup (the measurement results regarding the binding amounts of substances interacting with trypsin and the fluorescence intensities thereof).

Example 6

Selection of Compounds by Affinity

Using the SPR system used for screening shown in FIG. 1, immobilization of a ligand, the binding measurement of compounds, and selection of compounds were carried out.

(1) Production of a Sensor Chip

A cover glass with a size of 1 cm×1 cm, which had been coated with gold via evaporation resulting in a gold membrane with a thickness of 500 angstroms, was treated with a Model-208 UV-ozone cleaning system (TECHNOVISION INC.) for 30 minutes. Thereafter, it was placed in a spin coater (MODEL ASS-303; manufactured by ABLE) and then rotated at 1,000 rpm. 50 µl of a methyl ethyl ketone solution containing polymethyl methacrylate (2 mg/ml) was added dropwise to the center of the cover glass coated with gold via evaporation, and 2 minutes later, the rotation was terminated. The thickness of the membrane was measured by the ellipsometry method (In-Situ Ellipsometer MAUS-101; manufactured by Five Lab). As a result, the thickness of the polymethyl methacrylate membrane was found to be 200 angstroms. This sample is called a PMMA surface chip. This PMMA surface chip was immersed in an NaOH aqueous solution (1 N) at 40° C. for 16 hours, followed by washing with water 3 times. This sample is called a PMMA/COOH surface chip. This PMMA/COOH surface chip was immersed in 2 ml of a mixed solution of 1-ethyl-2,3-dimethylaminopropylcarbodiimide (400 mM) and N-hydroxysuccinimide (100 mM) for 60 minutes. Thereafter, it was immersed in 2 ml of an α-amino-polyethyleneoxy-ω-carboxylic acid (mean molecular weight: 5,000) aqueous solution (10 mM) for 16 hours. The resultant product was finally washed with water 5 times. The thus obtained sensor chip was used in the following operation.

(2) Immobilization of Trypsin

A mixed solution of 1-ethyl-2,3-dimethylaminopropylcarbodiimide (400 mM) and N-hydroxysuccinimide (100 mM) was added to the sensor chip produced in (1) above, followed by leaving at rest for 20 minute. Thereafter, the resultant product was washed with an HBS-N buffer containing 10 mM $CaCl_2$. Subsequently, trypsin (1 mg/ml, 10 mM $CaCl_2$-containing HBS-N buffer) was added thereto, followed by leaving at rest for 30 minutes. Thereafter, the resultant product was washed with a 10 mM $CaCl_2$-containing HBS-N buffer.

Thereafter, an ethanolamine/HCl solution (1M, pH 8.5) was added to the measurement chip, followed by washing with an HBS-N buffer (manufactured by Biacore).

By the aforementioned operations, trypsin was immobilized on the surface of the sensor chip via a covalent bond.

(2) Detection of Bond of Compounds

The sensor chip on which trypsin had been immobilized was washed with an HBS-N buffer. Thereafter, each of a leupeptin solution (2 μl), a nitrofurantoin solution (2 μl), and a chymostatin solution (2 μl) was added to the sensor chip at an SPR reader unit. After it was left at rest for 10 minutes, the amount by which resonance signals (RU value) had changed was defined as the amount of each compound binding to trypsin.

(3) Selection of Compounds

As shown in Table 1, leupeptin and nitrofurantoin, the binding of which were observed, were selected.

Example 7

Selection of Compounds Due to Biological Activity

Using the amount of the aforementioned compound binding to the sensor chip on which trypsin had been immobilized, the enzyme activity of trypsin was measured in the presence of the aforementioned compounds. Specifically, a substrate specific to trypsin (benzoyl-L-arginine-4-methylcoumarin-7-amide (hereinafter referred to as Bz-Arg-MCA); Peptide Institute, Inc.) was allowed to react with trypsin, and fluorescence in the decomposed product was measured.

(1) Reaction of Bz-Arg-MCA

Using the amount of the aforementioned compound binding to the trypsin-immobilized sensor chip produced in Example 6 (2), each of a mixed solution of a leupeptin solution (4 μM) and 0.2 mM Bz-Arg-MCA (1:1), a mixed solution of a nitrofurantoin solution (4 μM) and 0.2 mM Bz-Arg-MCA, and a 0.1 mM Bz-Arg-MCA solution, was added to the chip. Thereafter, the reaction was then carried out for 10, 30, 60, and 120 minutes.

(2) Fluorescence Measurement

Fluorescence measurement was carried out regarding the reaction for each of the aforementioned reaction times, using the BMGLabTechnologies FLUstar measurement device (excitation: 380 nm; and emission: 460 nm).

(3) Selection of Compounds

As shown in Table 2, leupeptin that inhibited the enzyme activity of trypsin was selected.

TABLE 2

| Compound | Binding amount (RU) | Selection due to binding amount | Measurement value of fluorescence intensity | Selection due to enzyme activity |
|---|---|---|---|---|
| None | — | — | 594 | — |
| Leupeptin | 23 | ○ | 3 | ○ |
| Nitrofurantoin | 12 | ○ | 588 | X |
| Chymostatin | 0 | X | — | — |

EFFECT OF THE INVENTION

The measurement method of the present invention enables two types of measurements, a binding reaction and an enzyme reaction, using a small amount of protein. In addition, by measuring activity according to the measurement method of the present invention, it becomes possible to determine whether or not the bound compound has bound to an active site. The screening method of the present invention enables two types of measurements, a binding reaction and an enzyme reaction, using a small amount of protein. In addition, by measuring activity according to the screening method of the present invention, it becomes possible to determine whether or not the bound compound has bound to an active site.

The invention claimed is:

1. A method for measuring the interaction of a physiologically active substance with a test substance and for measuring the biological activity of the physiologically active substance in the presence of the test substance using a biosensor, said method comprising:
    (1) contacting at least one test substance with a biosensor comprising a physiologically active substance immobilized on a substrate;
    (2) detecting or measuring the interaction between the physiologically active substance and said at least one test substance; and
    (3) measuring the biological activity of the physiologically active substance in the presence of said at least one test substance,
wherein, the detection and measurement of said at least one test substance interacting with said physiologically active substance and the measurement of the biological activity of said physiologically active substance are carried out in different steps.

2. The method according to claim 1, wherein the physiologically active substance is a protein.

3. The method according to claim 1, wherein the physiologically active substance is an enzyme.

4. The method according to claim 1, wherein the detection or measurement of said at least one test substance interacting with the physiologically active substance is carried out by surface plasmon resonance analysis.

5. The method according to claim 4, wherein the surface plasmon resonance analysis is carried out by using a biosensor used for a surface plasmon resonance measurement device comprising: a dielectric block; a metal film formed on a face of the dielectric block; a light source for generating a light beam; an optical system for allowing said light beam to enter said dielectric block such that total reflection conditions can be obtained at the interface between said dielectric block and said metal film and that components at various incident angles can be contained; and a light-detecting means for detecting the state of surface plasmon resonance by measuring the intensity of the light beam totally reflected at said interface, said biosensor being comprised of said dielectric block and said metal film, wherein said dielectric block is formed as one block comprising the entirety of the entrance face and exit face of said light beam and a face on which said metal film is formed, said metal film is integrated with the dielectric block.

6. The method according to claim 1, wherein the measurement of the biological activity of the physiologically active substance is carried out by spectroscopic measurement.

7. A method for screening a test substance for interaction with a physiologically active substance and for modification of the biological activity of said physiologically active substance, said method comprising:
(1) contacting at least one test substance with a biosensor comprising a physiologically active substance immobilized on a substrate,
(2) detecting the test substance interacting with said physiologically active substance by surface plasmon resonance analysis or local plasmon resonance analysis; and
(3) measuring the biological activity of said physiologically active substance in the presence of said at least one test substance.

8. The screening method according to claim 7, wherein 1 to 10 molecules of the test substances bind to a single molecule of the physiologically active substance.

9. The screening method according to claim 7, wherein the detection of a plurality of test substances by surface plasmon resonance analysis or local plasmon resonance analysis is carried out in a parallel detection approach.

10. The screening method according to claim 7, wherein the detection of said test substance interacting with said physiologically active substance and the measurement of the biological activity of said physiologically active substance are carried out in different steps.

11. The screening method according to claim 7, wherein said at least one test substance interacting with the physiologically active substance is detected by surface plasmon resonance analysis or local plasmon resonance analysis based on any of a binding amount, a binding constant, a binding rate constant, or a dissociation rate constant.

12. The screening method according to claim 7, wherein the biological activity of the physiologically active substance is indicated as any of a receptor activity level, an enzyme activity level, an antibody activity level, a metabolism activity level, a membrane potential, an ion emission level, or a gene expression level.

13. The screening method according to claim 7, wherein virtual screening is carried out on said at least one test substance before step (1), so as to reduce the number of test substances to be subjected to screening.

14. The screening method according to claim 7, wherein screening is automatically carried out using a screening device to which a standard value has previously been inputted, wherein said screening device is a device which detects the interaction of the said at least one test substance with the physiologically active substance by a change in surface plasmon resonance or local plasmon resonance and which detects a change in the biological activity of the physiologically active substance in the presence of the said at least one test substance.

* * * * *